US010604783B2

(12) United States Patent
Kim et al.

(10) Patent No.: US 10,604,783 B2
(45) Date of Patent: Mar. 31, 2020

(54) VIBRIO ASSAY METHODS AND KITS

(71) Applicants: Tae Jo Kim, Starkville, MS (US); Angelo DePaola, Coden, AL (US); Jessica L. Jones, Dauphin Island, AL (US)

(72) Inventors: Tae Jo Kim, Starkville, MS (US); Angelo DePaola, Coden, AL (US); Jessica L. Jones, Dauphin Island, AL (US)

(73) Assignee: Mississippi State University, Starkville, MS (US)

(*) Notice: Subject to any disclaimer, the term of this patent is extended or adjusted under 35 U.S.C. 154(b) by 0 days.

(21) Appl. No.: 14/503,001

(22) Filed: Sep. 30, 2014

(65) Prior Publication Data

US 2015/0093778 A1  Apr. 2, 2015

Related U.S. Application Data

(60) Provisional application No. 61/960,917, filed on Sep. 30, 2013.

(51) Int. Cl.
*C12Q 1/04* (2006.01)

(52) U.S. Cl.
CPC .......... *C12Q 1/045* (2013.01); *G01N 2333/28* (2013.01); *Y02A 50/451* (2018.01)

(58) Field of Classification Search
CPC ... C12Q 1/045; Y02A 50/451; G01N 2333/28
See application file for complete search history.

(56) References Cited

U.S. PATENT DOCUMENTS

| | | | |
|---|---|---|---|
| 4,308,347 A | 12/1981 | Forrer et al. | |
| 5,208,150 A | 5/1993 | Tate et al. | |
| 5,786,167 A | 7/1998 | Tuompo et al. | |
| 5,843,699 A | 12/1998 | Strenkoski et al. | |
| 6,136,554 A | 10/2000 | Bochner | |
| 2005/0244943 A1 | 3/2005 | Ladisch et al. | |
| 2011/0045470 A1 | 2/2011 | Murakami et al. | |
| 2013/0017569 A1 | 1/2013 | Martinez et al. | |

OTHER PUBLICATIONS

Canigral et al., Microbiological Research, 2010, vol. 165, p. 657-664.*
Hara-Kudo et al., Applied and Environmental Microbiology, 2001, vol. 67, No. 12, p. 5819-5823.*
Bhuiyan et al., Journal of Clinical Microbiology, 2003, vol. 41, No. 8, p. 3939-3941.*
Choopun et al., Applied and Environmental Microbiology, 2002, vol. 68, No. 2, p. 995-998.*
Difco and BBL Manual, 2nd Edition, 2009, p. 530 and 531 Only.*
Kaysner et al., Applied and Environmental Microbiology, 1994, vol. 60, No. 8, p. 3020-3022.*
Nakashima et al., Annals of Clinical and Laboratory Science, 2007, Vo. 37, No. 4, p. 330-334.*
Scott Sutton, The Most Probable Number Method and Its Uses in Enumeration, Qualification, and Validation, Journal of Validation Technology, (Summer 2010), pp. 35-38, vol. 16, No. 3, Institute of Validaton Technology, USA.

* cited by examiner

Primary Examiner — Kade Ariani
(74) Attorney, Agent, or Firm — Butler Snow LLP

(57) ABSTRACT

Methods and kits for detection of bacteria, especially *Vibrio parahaemolyticus* and *Vibrio vulnificus*, are provided using a unique combination of selective ingredients and two-phase culture (solid-phase culture gel and liquid-phase culture/enrichment broth) allows for high sensitivity and specificity of the kits for growth of *Vibrio parahaemolyticus* and *Vibrio vulnificus* in the detection methods and kits. The invention, through the detection mechanism accomplished by the novel formulation of selective ingredients and the two-phase culture, allows for real-time detection of a single cell of *Vibrio parahaemolyticus* and *Vibrio vulnificus* within 24±2 hours of introducing a target sample to the *Vibrio parahaemolyticus* and *Vibrio vulnificus* detection kits.

35 Claims, No Drawings

VIBRIO ASSAY METHODS AND KITS

CROSS-REFERENCES TO RELATED APPLICATIONS

This application claims the benefit of U.S. Provisional Application No. 61/960,917 by Kim, DePaola, and Jones, filed Sep. 30, 2013, which is incorporated herein by reference in its entirety.

STATEMENT REGARDING FEDERALLY SPONSORED RESEARCH OR DEVELOPMENT

This invention was made with Government support under 58-6402-2-729 awarded by the Agricultural Research Service, USDA and NA100AR4170078 awarded by the Department of Commerce, National Oceanic and Atmospheric Administration (NOAA). The Government has certain rights in the invention.

FIELD OF THE INVENTION

The present invention relates to the detection and quantification of the presence of pathogenic *Vibrio* in food and environment samples in laboratory, field or industrial settings with high sensitivity.

BACKGROUND OF THE INVENTION

The use of kits to detect certain *Vibrio* bacteria (sometimes referred to herein as *Vibrio* for brevity) in the environment, industrial settings, or on food is not a unique concept. U.S. Pat. No. 4,308,347 discloses a container device to detect pathogenic microorganisms in a fluid sample. The use of color generating chemicals was conceived as a mechanism to indicate the presence of pathogenic organisms with the intended result of a reduced need to use additional analysis equipment. U.S. Pat. No. 5,786,167 discloses a method to distinguish pathogen species such as those of *Salmonella* bacteria (sometimes referred to herein as *Salmonella* for brevity) by plating the sample on a solid medium of melibiose, mannitol, sorbitol, a pH indicator, and chromogenic substrate to reveal the presence of particular bacteria. If the test is positive, the bacteria is then cultivated and tested for additional indication for the presence of target pathogen specifically. U.S. Pat. No. 5,843,699 discloses a method of recognition and classification from a pre-enriched media that discourages the growth of non-target organisms while encouraging the growth of target microorganisms. The sample is then incubated and subjected to biochemical testing and analysis for results. To increase sensitivity, the prior art also discloses mechanisms to reduce the growth or generation of other bacteria within test samples, such as U.S. Pat. No. 5,208,150, which incorporates sodium salt to suppress the growth of competing organisms.

U.S. Pat. No. 6,136,554 discloses a method to detect *E. coli*, *Salmonella*, or a mixture of both by inoculating a nutrient medium into a sample and reviewing the color of bacterial colonies grown in the sample. If the result is negative, the process is repeated using a different biochemical tests for different bacteria.

*Vibrio* is the leading cause of food-borne illness from seafood consumption world-wide. Since 1996, a 400% increase in reported seafood-associated illnesses in the U.S. Current methods to detect and quantify *Vibrio* are so laborious and expensive that few laboratories in the world have analytical capabilities to produce reliable results, and the capacity at labs that do is very limited. More analytical resources are needed to monitor the coastal environment and seafood supply (e.g., surge resources in the event of an outbreak and mitigation resources for sample monitoring and validation of present post-harvest processing techniques). The prior art does not disclose a culture-based mechanism or kit to detect and quantify the presence and amount of pathogenic *Vibrio* at a high-sensitivity rate, that is more accurate, that significantly reduces the occurrence of Type-I or Type-II errors such as false-positives and false-negatives, that can be performed in a significantly reduced time period, that can be accurate and reproducible without the use of additional laboratory machinery or equipment, and that can be performed through a single-tube methodology.

Therefore, a need in the art for *Vibrio* assay kits with the previously mentioned attributes is evident.

SUMMARY OF THE INVENTION

The invention provides a series of detection methods and novel *Vibrio* assay kits useful for detecting and quantifying the presence of selected *Vibrio* populations or species in food and environment samples in laboratory, field or industrial settings with a high sensitivity. The invention provides a simple, inexpensive mechanism to detect and quantify *Vibrio* in food and environment samples with a very high sensitivity while also preventing the occurrence of false-positives, false-negatives, or other statistical errors. A novel combination of selective ingredients is utilized to allow the growth of *Vibrio* in the assay kits and to enhance the physiological activities of cell motility/infusion and enzyme production of *Vibrio* under facultative anaerobic conditions. The invention, through the detection mechanism accomplished by the novel combination of selective ingredients, allows for real-time detection of a single cell of *Vibrio* within 24 hours or less of introducing a pre-enriched sample to the *Vibrio* assay kits. An additional benefit of this invention is that it does not require the use of additional machinery or equipment to detect the presence of pathogenic *Vibrio* in the test sample. The invention does not require additional machinery or equipment to read or interpret the results of the detection mechanism, unlike the current state of technology.

It is the object of this invention to provide a method and kit to detect *Vibrio* in food and environment samples, in laboratory, and industrial settings, through the use of *Vibrio* assay kits. It is an additional object of this invention to describe a methodology for detecting *Vibrio* in food and environment samples in a *Vibrio* assay kit that reduces the opportunity for Type-I or Type-II errors while also limiting the time and additional resources traditionally required for detecting the presence of *Vibrio*.

The invention relies on a unique combination of selective/non-selective media, chemicals, temperature, and biomarker activities of *Vibrio* that promote the facultative anaerobic growth and migration of *Vibrio* while also inhibiting the growth of other microorganisms. For example, bile salt and antibiotics such as colistin sulfate salt and polymyxin B sulfate are examples of biological chemicals that are known in the industry to increase selectivity of *Vibrio* at the exclusion of other microorganisms. Utilizing the combination of these selective media and chemicals, the disclosed *Vibrio* assay kit can quickly increase selectivity of *Vibrio* in a test sample; this enhanced selectivity can then be evaluated and evidenced through the assay kits by altering the characteristics of a signal indicator-containing medium, such as bromothymol blue, phenol red, esculin, and ferric ammonium sulfate as signal indicators which, in turn, will provide visible evidence of the presence of pathogenic *Vibrio*.

DETAILED DESCRIPTION

The following detailed description is presented to enable any person skilled in the art to make and use the invention. For purposes of explanation, specific details are set forth to provide a thorough understanding of the present invention. However, it will be apparent to one skilled in the art that these specific details are not required to practice the invention. Descriptions of specific applications are provided only as representative examples. Various modifications to the preferred embodiments will be readily apparent to one skilled in the art, and the general principles defined herein may be applied to other embodiments and applications without departing from the scope of the invention. The present invention is not intended to be limited to the embodiments described, but is to be accorded the widest possible scope consistent with the principles and features disclosed herein.

The invention provides a detection method and a novel *Vibrio* assay kit useful for detecting and quantifying the presence of *Vibrio* in food, especially in seafood, and more specifically in the shellfish supply (e.g., oysters, crabs, and prawns), and environmental samples in laboratory, field, or industrial settings with a high sensitivity. The invention provides a simple, inexpensive mechanism to detect and quantify *Vibrio* in food and environmental samples with a very high sensitivity while also preventing the occurrence of false-positives, false-negatives, or other statistical errors. A novel combination of selective ingredients is utilized to allow the growth of *Vibrio* in the assay kits and to enhance the physiological activities of cell motility/infusion and enzyme production of *Vibrio* under facultative anaerobic conditions. The invention, through the detection mechanism accomplished by the novel combination of selective ingredients, allows for real-time detection of as few as a single cell of *Vibrio* within 24 hours or less of inoculating the test vessel of a *Vibrio* assay kit that includes a pre-enriching liquid-phase media. An additional benefit of this invention is that it does not require the use of additional machinery or equipment to detect the presence of pathogenic *Vibrio* in the test sample, such as expensive real-time PCR equipment and consumable reagents.

The disclosed invention provides methods and kits to detect *Vibrio* in food and environment samples, in laboratory, and industrial settings, through the use of *Vibrio* assay kits. The disclosed invention also provides a methodology for detecting *Vibrio* in food and environment samples in a *Vibrio* assay kit that reduces the opportunity for Type-I or Type-II errors while also limiting the time and additional resources traditionally required for detecting the presence of *Vibrio*, such as culture methods that require several culturing steps to obtain culture identification or molecular methods, including DNA probes and PCR. In a preferred embodiment, alkaline peptone water as a liquid-phase media increases the sensitivity of the *Vibrio* assay vessels (reducing Type-II errors) to detect *Vibrio vulnificus* and *Vibrio parahaemolyticus*. To reduce Type-I errors, a solid-phase media is used in preferred embodiments: (a) *Vibrio vulnificus* in a solid-phase media express an enzyme that allows for hydrolyzing esculin, while antibiotics (colistin and polymyxin B) and bile salt inhibit other bacteria at high pH; (b) *Vibrio parahaemolyticus* in a solid-phase media produce acid from arabinose fermentation, while bile salt inhibits other bacteria at high pH; and (c) pathogenic *Vibrio parahaemolyticus* in a solid-phase media produce an enzyme that allows for utilizing urea to increase pH of the solid-phase media, while bile salt inhibits other bacteria.

The invention relies on a unique combination of selective/non-selective media, chemicals, temperature, and biomarker activities of *Vibrio* that promote the facultative anaerobic growth and migration from liquid-phase media to solid-phase media of *Vibrio* while also inhibiting the growth of other microorganisms. For example, bile salt and antibiotics such as colistin sulfate salt and polymyxin B sulfate are examples of biological chemicals that are known in the industry to increase selectivity of *Vibrio* at the exclusion of other microorganisms. Utilizing the combination of these selective media and chemicals, the disclosed *Vibrio* assay kit can quickly increase selectivity of *Vibrio* in a test sample; this enhanced selectivity can then be evaluated and evidenced through the assay kits by altering the characteristics of a signal indicator-containing medium, such as bromothymol blue, phenol red, esculin, and ferric ammonium sulfate as signal indicators which, in turn, will provide visible evidence of the presence of pathogenic *Vibrio*.

The following provides detailed descriptions of the methods and kits to detect arabinose and urea-positive *Vibrio parahaemolyticus* ("Vp") and esculin-hydrolysable *Vibrio vulnificus* ("Vv") in food and environment samples and in laboratory and industrial settings, through the use of *Vibrio* assay kits.

A single-tube biphasic culture assay system is provided with sufficient specificity for the identification and detection of either Vp or Vv in complex matrices, such as seafood, which also contains interfering bacteria that mimic these pathogens.

The system combines broth enrichment and selective isolation/identification into a single-tube assay methodology that can provide accurate screening results in about 24 hours from inoculation. The alkaline peptone water or similar enrichment broth added to test vessels is formulated to have optimal pH and NaCl concentrations to select for the target *Vibrio* bacteria in the given assay. Compounds that enhance the recovery of stressed or injured cells may also be included in this phase to optimize the sensitivity and recovery, including peptone and sodium chloride. The solid phase will suppress growth of background microflora by incorporation of antimicrobial compounds and differential aspects will be achieved based on the unique biochemical utilization patterns of Vv and Vp with indicator compounds and dyes. Advanced molecular methods, such as real-time PCR, are available, but are very expensive and laborious (require specially-trained personnel and expensive equipment and consumable reagents). The low cost and simplicity of the disclosed elegant solution allows for rapid implementation and maintained monitoring of the coastal environment and seafood supply.

Preparation of the Vp Arabinose Agar Kit Vessel (A Preferred Embodiment)

1. A volume of bottom agar is prepared by boiling 3% NaCl, 1% peptone, 1% agar, 1% arabinose, and 1% sodium citrate in distilled water until agar granules are completely melted.

2. Bile salt (0.5%) and bromothymol blue solution (1%) (0.6% bromothymol blue stock in 70% ethyl alcohol) are added. The final pH (8.4-8.9) is adjusted by adding 10N NaOH into the boiled agar media.

3. Then, the agar is cooled to approximately 50° C.

4. In laboratory studies, 1000 μL of bottom agar media is placed in sterile 96-well assay block (2 mL) and cooled to approximately 50° C. at room temperature until solidified.

5. Top agar is prepared by boiling 1% peptone, 1% NaCl, and 1% agar until agar granules are completely melted. The pH (8.4-8.9) is adjusted by adding 10N NaOH and cooled to approximately 50° C.

6. The cooled top agar media (100 μL) is placed on pre-filled bottom agar and cooled at room temperature until solidified.

7. Before inoculation of samples, 500 μL of alkaline peptone water (~pH 8.6) is filled on the Vp arabinose agar assay kit vessel.

8. The Vp arabinose agar assay kit vessel is now prepared for use. The individual assay formulations (including top agar and bottom agar but not bile salt and alkaline peptone water) can be stored separately under standard operating procedures and conditions; and then combined before use as provided above.

As alternative formulations of Vp arabinose media, there are other embodiments (i.e., other agar or solid phase/gelling agent mixtures, selective media, chemicals, volume, and concentration, etc.) of the invention. Peptone, agar, arabinose, sodium citrate, bile salt, sodium hydroxide, and bromothymol blue are used in one preferred embodiment of the invention. However, other alternative selective solid or semi-solid media can be used. For example, in another preferred embodiment, pectin or gelatin with calcium chloride or magnesium chloride is used in place of agar to significantly reduce preparation time and expense. Depending on the desired matrix properties of the solid-phase gel, these can each be used in concentrations of from 0.01% to 10%. In a more preferred embodiment, low methoxyl pectin with calcium chloride or magnesium chloride from 0.01% to 10% is used in place of agar (see below for Preparation of the Vp Arabinose Pectin Kit). Other modification examples include, but are not limited to, a mixture of proteose peptone, peptic digest of animal tissue, pancreatic digest of casein, gelatin, starch, disodium phosphate, yeast extract, lactose, saccharose, sodium chloride, agar, gelatin, pectin, brilliant green, crystal violet, and phenol red or other pH indicators including brilliant yellow, neutral red, cresol red, curcumin, m-nitrophenol, bromothymol blue, or m-cresol red/purple can be used. Commercially available selective media such as thiosulfate-citrate-bile salts-sucrose agar (TCBS) could be used for alternative selective solid or semi-solid media.

Preparation of the Vp Arabinose Pectin Kit Vessel (A Preferred Embodiment)

1. A volume of bottom soft gel media is prepared by boiling 3% NaCl, 1% peptone, 0.01-0.5% agar, 1% arabinose, and 1% sodium citrate in distilled water until agar is completely melted and dissolved. Preferably, 0.25% agar is used in the bottom soft gel media.

2. Bile salt (0.5%) and bromothymol blue solution (1%) (0.6% bromothymol blue stock in 70% ethyl alcohol) are added. The final pH (8.4-8.9) is adjusted by adding 10N NaOH into the bottom soft gel media.

3. In laboratory studies, when the bottom soft gel media is cool, 1000 μL of bottom soft gel media is placed in sterile 96-well assay block (2 mL).

4. Top pectin media is prepared by heating 1% peptone, 1% NaCl, and 1.5% low methoxyl pectin until pectin is completely dissolved. The pH (8.4-8.9) is adjusted by adding 10N NaOH.

5. The top pectin media (100 μL) is placed on pre-filled bottom soft gel media and kept at room temperature.

6. 2% calcium chloride (100 μL total–50 μL on each of two side walls of the vessels) is added to the top pectin media to gel the pectin.

7. Before inoculation of samples, 500 μL of alkaline peptone water (~pH 8.6) is filled on the Vp arabinose pectin assay kit vessel.

8. The Vp arabinose pectin assay kit vessel is now prepared for use. The individual assay formulations (including top pectin media, bottom soft gel media, and calcium chloride, but not alkaline peptone water) can be stored separately under standard operating procedures and conditions; and then combined before use as provided above.

The alternative formulations of Vp arabinose media described above for the agar kits may also be used to supplement or modify the pectin kits.

Preparation of the Vp Urea Agar Kit (A Preferred Embodiment)

1. A volume of bottom agar is prepared by boiling 3% NaCl, 0.1% peptone and 1% agar in distilled water until agar granules are completely melted.

2. Urea (1%), bile salt (0.5%), and phenol red (0.0125%; of 1% phenol red sodium salt stock in distilled sterilized water) is completely dissolved in boiled agar media.

3. Then, the agar media is cooled to approximately 50° C.

4. In laboratory studies, 500 μL of bottom agar media is placed in sterile 96-well assay block (2 mL) and cooled at room temperature until solidified.

5. Top agar is prepared by boiling 1% peptone, 1% NaCl, 1% agar, 0.95% dipotassium hydrogen phosphate dibasic, and 0.91% potassium dihydrogen phosphate monobasic until agar granules are completely melted.

6. The cooled top agar media (150 μL) is placed on pre-filled bottom agar and cooled at room temperature until solidified.

7. Before inoculation of samples, 500 μL of alkaline peptone water (~pH 8.6) is filled on the Vp urea agar assay kit vessel.

8. The Vp urea agar assay kit vessel is now prepared for use. The assay formulations (including top agar and bottom agar but not urea, bile salt, and alkaline peptone water) can be stored separately under standard operating procedures and conditions; and then combined before use as provided above.

As alternative formulations of Vp urea media, there are other embodiments (i.e., other agar or solid phase/gelling agent mixtures, selective media, chemicals, volume and concentration etc.) of the invention. Peptone, agar, urea, NaCl, bile salt, potassium dihydrogen phosphate monobasic, and dipotassium hydrogen phosphate dibasic are used in one preferred embodiment of the invention. However, other alternative selective solid or semi-solid media can be used. For example, in another preferred embodiment, pectin or gelatin with calcium chloride or magnesium chloride is used in place of agar to significantly reduce preparation time and expense. Depending on the desired matrix properties of the solid-phase gel, these can each be used in concentrations of from 0.01% to 10%. In a more preferred embodiment, low methoxyl pectin with calcium chloride or magnesium chloride from 0.01% to 10% is used in place of agar (see below for Preparation of the Vp Urea Pectin Kit). Other modification examples include, but are not limited to, a mixture of proteose peptone, peptic digest of animal tissue, pancreatic digest of casein, gelatin, starch, disodium phosphate, yeast extract, lactose, saccharose, sodium chloride, agar, gelatin, pectin, brilliant green, crystal violet, sodium sulfapyridine, and phenol red or other pH indicators including brilliant yellow, neutral red, cresol red, curcumin, m-nitrophenol, bromothymol blue, or m-cresol red/purple can be used. Commercially available selective media such as a urea media could be used for alternative selective solid or semi-solid media.

Preparation of the Vp Urea Pectin Kit Vessel (A Preferred Embodiment)

1. A volume of bottom soft gel media is prepared by boiling 3% NaCl, 0.1% peptone, and 0.01-0.5% agar in distilled water until agar is completely melted and dissolved. Preferably, 0.25% agar is used in the bottom soft gel media.

2. Urea (1%), bile salt (0.5%), and phenol red (0.0125%; of 1% phenol red sodium salt stock in distilled sterilized water) is added and completely dissolved in the boiled soft gel media.

3. In laboratory studies, 500 μL of bottom soft gel media is placed in sterile 96-well assay block (2 mL) and kept at room temperature.

4. Top pectin media is prepared by boiling 1% peptone, 1% NaCl, and 1.5% low methoxyl pectin, 0.95% dipotassium hydrogen phosphate dibasic, and 0.91% potassium dihydrogen phosphate monobasic until pectin is completely dissolved.

5. The top pectin media (150 μL) is placed on pre-filled bottom soft gel media and kept at room temperature.

6. 2% calcium chloride (100 μL total–50 μL on each of two side walls of the vessels) is added to the top pectin media to gel the pectin.

7. Before inoculation of samples, 500 μL of alkaline peptone water (~pH 8.6) is filled on the Vp urea pectin assay kit vessel.

8. The Vp urea pectin assay kit vessel is now prepared for use. The assay formulations (including top pectin and bottom soft gel media, but not urea, bile salt, and alkaline peptone water) can be stored separately under standard operating procedures and conditions; and then combined before use as provided above.

The alternative formulations of Vp urea media described above for the agar kits may also be used to supplement or modify the pectin kits.

Preparation of the Vv Agar Kit Vessel (A Preferred Embodiment)

1. A volume of bottom agar is prepared by boiling 1% NaCl, 1% proteose peptone #3, 1.5% cellobiose, 1% agar, 0.3% esculin, and 0.05% ferric ammonium citrate in distilled water until agar granules are completely melted and then autoclaved for 15 min at 121° C. and 15 psi.

2. The pH (8.2-9.2) is adjusted by adding 10N NaOH.

3. After autoclave, the bottom agar is cooled to approximately 50° C.

4. In laboratory studies, 300 μL of bottom agar is placed in sterile 96-well assay block (2 mL) and cooled at room temperature until solidified.

5. Middle agar is prepared by boiling 1% NaCl, 1% proteose peptone #3, 1.5% cellobiose, and 1% agar until agar granules are completely melted and then autoclaved for 15 min at 121° C. and 15 psi.

6. Right after autoclaving, bile salt (0.6%) is added and solubilized in hot middle agar.

7. The pH (8.2-9.2) is adjusted by adding 10N NaOH.

8. When the middle agar media with bile salt is cooled to approximately 48-49° C., colistin sulfate salt (0.0001%, >15000 USP units/mg) and polymyxin B sulfate (0.0001%, >6000 USP units/mg) are then added.

9. Then, the middle agar media (400 μL) is placed on pre-filled bottom agar and cooled at room temperature until solidified.

10. Top agar is prepared by boiling 1% NaCl, 1% proteose peptone #3, 1.5% cellobiose, and 1% agar until agar granules are completely melted and then autoclaved for 15 min at 121° C. and 15 psi.

11. The pH (8.2-9.2) is adjusted by adding 10N NaOH.

12. Top agar (100 μL) is placed on pre-filled middle and bottom agars and cooled at room temperature until solidified.

13. Before inoculation of samples, 500 μL of alkaline peptone water (~pH 8.6) is filled on the Vv agar assay kit vessel.

14. The Vv agar assay kit vessel is now prepared for use. The assay formulations (including top agar, bottom agar, and middle agar but not antibiotics, bile salt, and alkaline peptone water) can be stored separately under standard operating procedures and conditions; and then combined before use.

As alternative formulations of Vv assay kit, there are other embodiments (i.e., other agar or solid phase/gelling agent mixtures, selective media, chemicals, volume, and concentration, etc.) of the invention. Peptone, agar, arabinose, sodium citrate, bile salt, sodium hydroxide, and bromothymol blue are used in one preferred embodiment of the invention. However, other alternative selective solid or semi-solid media can be used. For example, in another preferred embodiment, pectin or gelatin with calcium chloride or magnesium chloride is used in place of agar to significantly reduce preparation time and expense. Depending on the desired matrix properties of the solid-phase gel, these can each be used in concentrations of from 0.01% to 10%. In a more preferred embodiment, low methoxyl pectin with calcium chloride or magnesium chloride from 0.01% to 10% is used in place of agar (see below for Preparation of the Vv Pectin Kit). Other modification examples include, but are not limited to, a mixture of proteose peptone, peptic digest of animal tissue, pancreatic digest of casein, gelatin, starch, disodium phosphate, yeast extract, lactose, saccharose, sodium chloride, agar, gelatin, pectin, brilliant green, crystal violet, sodium sulfapyridine, other antibiotics, and phenol red or other pH indicators including brilliant yellow, neutral red, cresol red, curcumin, m-nitrophenol, bromothymol blue, or m-cresol red/purple can be used. Commercially available selective media such as urea media could be used for alternative selective solid or semi-solid media.

Preparation of the Vv Pectin Kit Vessel (A Preferred Embodiment)

1. A volume of bottom pectin is prepared by boiling 1% NaCl, 1% proteose peptone #3, 1.5% cellobiose, 1% low methoxyl pectin, 0.3% esculin, and 0.05% ferric ammonium citrate in distilled water until pectin is completely dissolved and then autoclaved for 15 min at 121° C. and 15 psi.

2. The pH (8.2-9.2) is adjusted by adding 10N NaOH.

3. After autoclave, the bottom pectin media is cooled at room temperature.

4. 300 μL of bottom pectin media is placed in sterile 96-well assay block (2 mL).

5. 2% calcium chloride (100 μL total−50 μL on each of two side walls of the vessels) is added to the bottom pectin media to gel the pectin.

6. Middle pectin media is prepared by boiling 1% NaCl, 1% proteose peptone #3, 1.5% cellobiose, and 1% low methoxyl pectin until pectin is completely dissolved and then autoclaved for 15 min at 121° C. and 15 psi.

7. Right after autoclaving, bile salt (0.6%) is added and solubilized in hot middle pectin media.

8. The pH (8.2-9.2) is adjusted by adding 10N NaOH.

9. When the middle pectin media with bile salt is cooled to approximately 48-49° C., colistin sulfate salt (0.0001%, >15000 USP units/mg) and polymyxin B sulfate (0.0001%, >6000 USP units/mg) are then added.

10. Then, the middle pectin media (400 μL) is placed on pre-filled bottom pectin media and cooled at room temperature.

11. 2% calcium chloride (100 μL total–50 μL on each of two side walls of the vessels) is added to the middle pectin media to gel the pectin.

12. Top pectin media is prepared by boiling 1% NaCl, 1% proteose peptone #3, 1.5% cellobiose, and 1% low methoxyl pectin until the pectin is completely dissolved and then autoclaved for 15 min at 121° C. and 15 psi.

13. The pH (8.2-9.2) is adjusted by adding 10N NaOH.

14. The top pectin media (100 μL) is placed on pre-filled middle and bottom pectin media and kept at room temperature.

15. 2% calcium chloride (100 μL total–50 μL on each of two side walls of the vessels) is added to the top pectin media to gel the pectin.

16. Before inoculation of samples, 500 μL of alkaline peptone water (~pH 8.6) is filled on the Vv pectin assay kit vessel.

17. The Vv pectin assay kit vessel is now prepared for use. The assay formulations (including top pectin, bottom pectin, and middle pectin, but not antibiotics, bile salt, and alkaline peptone water) can be stored separately under standard operating procedures and conditions; and then combined before use.

The alternative formulations of Vv media described above for the agar kits may also be used to supplement or modify the pectin kits.

*Vibrio* Assay Kits

The present invention relates to novel *Vibrio* assay kits comprised of a novel combination of selective ingredients that can be used to detect and/or quantify the population of pathogenic *Vibrio* present in a test sample. The *Vibrio* test kits include, but are not limited to, the following: instructions for storage, use, and detection/quantification; assay block/vessel(s); non-selective pre-enrichment liquid media; selective solid or semi-solid media; selective liquid media; and color chart to read sample.

The *Vibrio* assay kits would include at least one vessel (*Vibrio* detection assay vessel for detecting the presence of a *Vibrio* bacteria), including singular or a plurality of test tubes, blocks, or other culture vessels, whereby each *Vibrio* detection assay vessel contains a biochemicals for the detection mechanism (signal indicator) in a stable matrix coupled with a growth medium in a single vessel also in a stable matrix. For example, a *Vibrio* detection assay vessel may include microplates, test tubes of various sizes, culture blocks, etc. The *Vibrio* test kit also includes a specific set of instructions, which may include directions for storage, use, and detection reading. The *Vibrio* kit may also contain a color chart specific to the signal indicator-containing medium provided or prepared by the user. The *Vibrio* test kit could be sold on an individual or bulk basis and could be incorporated to include components necessary to perform the steps or processes common to the process of obtaining a viable sample from the environment, industrial setting, or food sample, especially seafood (e.g., raw and post-harvest processed oysters, crabs, and prawns).

*Vibrio* Assay Kit Methods

Step 1 (Inoculation/Incubation): Test samples are taken in accordance with normal and well-known laboratory and industrial setting procedures. Test samples of an appropriate dilution(s) are inoculated in the appropriately prepared *Vibrio* assay kits and incubated at 35-37° C. for a period of 18-24 hours. For quantification, replicates of serial dilutions are inoculated and incubated in Step 1 following well-known procedures for most probable number analysis (see, e.g., Scott Sutton, *The Most Probable Number Method and Its Uses in Enumeration, Qualification, and Validation*, J. Valid. Tech. vol. 16, no. 3 (Summer 2010), which is hereby incorporated by reference in its entirety). For example, but without limitation, dilutions can be log base 10 or log base 2.

Step 2 (Reading): After incubation, the *Vibrio* detection kits are exposed to light and the resulting color change, if any, in the kit is observed and used to indicate the presence of a specific pathogenic *Vibrio* species:

- Vp arabinose kit positive shows yellow color and negative shows blue/green and other colors;
- Vp urea kit positive shows pink color and negative shows yellow and other colors; and
- Vv kit positive shows black color and negative shows yellow/brown and other colors.

The terms "comprising," "including," and "having," as used in the claims and specification herein, shall be considered as indicating an open group that may include other elements not specified. The terms "a," "an," and the singular forms of words shall be taken to include the plural form of the same words, such that the terms mean that one or more of something is provided. The term "one" or "single" may be used to indicate that one and only one of something is intended. Similarly, other specific integer values, such as "two," may be used when a specific number of things is intended. The terms "preferably," "preferred," "prefer," "optionally," "may," and similar terms are used to indicate that an item, condition or step being referred to is an optional (not required) feature of the invention.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims. It will be apparent to one of ordinary skill in the art that methods, devices, device elements, materials, procedures, and techniques other than those specifically described herein can be applied to the practice of the invention as broadly disclosed herein without resort to undue experimentation. For example, such modifications as additional or different color-indicating interactions, materials, chemicals, gradient layers, concentration of materials, pH of all solid, semi-solid and liquid media, size/volume of vessels such as microplates and material of vessels could be used. All art-known functional equivalents of methods, devices, device elements, materials, procedures, and techniques described herein are intended to be encompassed by this invention. Whenever a range is disclosed, all subranges and individual values are intended to be encompassed. This invention is not to be limited by the embodiments disclosed, including any exemplified in the specification, which are given by way of example and not of limitation.

All references throughout this application, for example patent documents including issued or granted patents or equivalents, patent application publications, and non-patent literature documents or other source material, are hereby incorporated by reference herein in their entireties, as though individually incorporated by reference, to the extent each reference is at least partially not inconsistent with the disclosure in the present application (for example, a reference that is partially inconsistent is incorporated by reference except for the partially inconsistent portion of the reference).

We claim:

1. A *Vibrio* detection assay vessel for detecting the presence of a target *Vibrio* bacteria consisting essentially of: at least one solid-phase gel medium and a matrix material allowing facultative anaerobic growth of the target *Vibrio* bacteria, a liquid-phase medium, and a visible signal indicator within the at least one solid-phase gel medium disposed in a single culture vessel; wherein the at least one solid-phase gel medium reduces false-positive errors in detecting *Vibrio* bacteria and suppresses growth of non-target bacteria and wherein the liquid-phase medium increases the sensitivity of the *Vibrio* bacteria detection assay vessels evidenced by altering the characteristics of said signal indicator within the at least one solid phase medium reduces false-negative errors in detecting *Vibrio* bacteria and enhance growth of the target *Vibrio* bacteria; further wherein the target *Vibrio* bacteria detected within 24 hours or less of inoculating the single culture vessel without the use of additional machinery or equipment is selected from the group consisting of *Vibrio parahaemolyticus* and *Vibrio vulnificus*.

2. The *Vibrio* detection assay vessel of claim 1, wherein the target *Vibrio* bacteria detected is *Vibrio parahaemolyticus*.

3. The *Vibrio* detection assay vessel of claim 2, wherein the at least one solid-phase gel medium is a bottom solid-phase gel medium that comprises arabinose.

4. The *Vibrio* detection assay vessel of claim 3, wherein the visible signal indicator is bromothymol blue.

5. The *Vibrio* detection assay vessel of claim 2, wherein the at least one solid-phase gel medium is a bottom solid-phase gel medium that comprises urea.

6. The *Vibrio* detection assay vessel of claim 5, wherein the visible signal indicator is phenol red.

7. The *Vibrio* detection assay vessel of claim 1, wherein the target *Vibrio* bacteria detected is *Vibrio vulnificus*.

8. The *Vibrio* detection assay vessel of claim 7, wherein the at least one solid-phase gel medium is a bottom solid-phase gel medium that comprises esculin.

9. The *Vibrio* detection assay vessel of claim 8, wherein the visible signal indicator is ferric ammonium citrate.

10. The *Vibrio* detection assay vessel of claim 1, wherein the at least one solid-phase gel medium comprises agar as the matrix material allowing mobility and facultative anaerobic growth of the target *Vibrio* bacteria.

11. The *Vibrio* detection assay vessel of claim 1, wherein the at least one solid-phase gel medium comprises pectin as the matrix material allowing mobility and facultative anaerobic growth of the target *Vibrio* bacteria.

12. The *Vibrio* detection assay vessel of claim 1, wherein the liquid-phase medium comprises alkaline peptone water at about pH 8.6.

13. A method of detecting a target *Vibrio* bacteria comprising:
    (a) inoculating the liquid-phase medium of at least one *Vibrio* detection assay vessel of claim 1 with a sample suspected of harboring the target *Vibrio* bacteria;
    (b) incubating the inoculated vessel of step (a) for about 24 hours at 35-37° C. under facultative anaerobic conditions; and
    (c) reading the incubated vessel of step (b) for a visible signal indicator for the presence or absence of the target *Vibrio* bacteria after facultative anaerobic growth.

14. The method of claim 13, wherein the target *Vibrio* bacteria detected is *Vibrio parahaemolyticus*.

15. The method of claim 13, wherein the target *Vibrio* bacteria detected is *Vibrio vulnificus*.

16. A kit for detecting the presence of a target *Vibrio* bacteria comprising at least one *Vibrio* detection assay vessel of claim 1 and instructions.

17. The kit of claim 16, wherein the at least one *Vibrio* detection assay vessel is prepackaged with prepared medium for the at least one solid-phase gel medium and the liquid-phase medium.

18. The kit of claim 16, wherein the at least one *Vibrio* detection assay vessel is prepackaged as components for a user to prepare medium for the at least one solid-phase gel medium and the liquid-phase medium.

19. The kit of claim 18, wherein the instructions comprise directions for a user to prepare said *Vibrio* detection assay vessel.

20. The kit of claim 16, wherein the target *Vibrio* bacteria detected is *Vibrio parahaemolyticus*.

21. The kit of claim 20, wherein the at least one solid-phase gel medium is two solid-phase gel medium comprising a bottom solid-phase gel medium and a top solid-phase gel medium, and wherein the bottom solid-phase gel medium comprises arabinose.

22. The kit of claim 21, wherein the bottom solid-phase gel medium further comprises the visible signal indicator which is bromothymol blue.

23. The kit of claim 21, wherein the bottom solid-phase gel medium further comprises bile salt.

24. The kit of claim 20, wherein the at least one solid-phase gel medium is two solid-phase gel medium comprising a bottom solid-phase gel medium and a top solid-phase gel medium, and wherein the bottom solid-phase gel medium comprises urea.

25. The kit of claim 24, wherein the bottom solid-phase gel medium further comprises the visible signal indicator which is phenol red.

26. The kit of claim 24, wherein the bottom solid-phase gel medium further comprises bile salt.

27. The kit of claim 16, wherein the target *Vibrio* bacteria detected is *Vibrio vulnificus*.

28. The kit of claim 27, wherein the at least one solid-phase gel medium is three solid-phase gel medium comprising a bottom solid-phase gel medium, a middle solid-phase gel medium, and a top solid-phase gel medium, and wherein the bottom solid-phase gel medium comprises esculin.

29. The kit of claim 28, wherein the bottom solid-phase gel medium further comprises the visible signal indicator which is ferric ammonium citrate.

30. The kit of claim 28, wherein the middle solid-phase gel medium comprises at least antibiotic that suppresses non-target bacteria.

31. The kit of claim 30, wherein the at least one antibiotic is two antibiotics consisting of colistin sulfate and polymyxin B sulfate.

32. The kit of claim 28, wherein the bottom solid-phase gel medium further comprises bile salt.

33. The kit of claim 16, wherein the at least one solid-phase gel medium comprises agar as the matrix material allowing mobility and facultative anaerobic growth of the target *Vibrio* bacteria.

34. The kit of claim 16, wherein the at least one solid-phase gel medium comprises pectin as the matrix material allowing mobility and facultative anaerobic growth of the target *Vibrio* bacteria.

35. The kit of claim 16, wherein the liquid-phase medium comprises alkaline peptone water at about pH 8.6.

* * * * *